(12) United States Patent
Lewis

(10) Patent No.: US 7,901,413 B1
(45) Date of Patent: Mar. 8, 2011

(54) SURGICAL LOCKING SCREW AND DRIVER ARRANGEMENT

(75) Inventor: David H. Lewis, Fort Collins, CO (US)

(73) Assignee: High Plains Technology Group, LLC, Fort Collins, CO (US)

( * ) Notice: Subject to any disclaimer, the term of this patent is extended or adjusted under 35 U.S.C. 154(b) by 708 days.

(21) Appl. No.: 11/490,337

(22) Filed: Jul. 21, 2006

(51) Int. Cl.
*A61B 17/58* (2006.01)
*A61B 17/60* (2006.01)
*A61F 2/00* (2006.01)

(52) U.S. Cl. .......................................... 606/104; 411/406

(58) Field of Classification Search ................ 606/96, 606/104, 264–279, 300–321, 86 A, 99, 1–4; 433/141, 174; 411/402–407
See application file for complete search history.

(56) References Cited

U.S. PATENT DOCUMENTS

| | | | | | |
|---|---|---|---|---|---|
| 2,905,215 | A | * | 9/1959 | Hlynsky | 81/455 |
| 4,497,225 | A | * | 2/1985 | Vaughn | 81/451 |
| 5,353,667 | A | * | 10/1994 | Wilner | 81/436 |
| 2005/0169729 | A1 | * | 8/2005 | Nowak | 411/402 |

* cited by examiner

*Primary Examiner* — Eduardo C Robert
*Assistant Examiner* — Christina Negrelli
(74) *Attorney, Agent, or Firm* — Santangelo Law Offices, P.C.

(57) ABSTRACT

A surgical screw and driver arrangement whereby the end of the driver is vertically inserted and removed from the slotted end of the surgical screw and whereby the end of the driver is attached to and removed from the slotted end of the surgical screw by a quarter turn in the clockwise and counterclockwise directions.

The driver includes an inner shaft connecting with a center locking cam at one end of the driver and an outer shaft that connects with a pair of blades, one on each side of the locking cam.

The surgical screw includes a slotted head at one end and a tapered threaded rod attached to the head. A pair of dovetail slots extending perpendicular within the slotted head receives the locking cam when the driver inner shaft is rotated a quarter turn clockwise to fasten the surgical screw to the end of the driver.

2 Claims, 4 Drawing Sheets

SURGICAL LOCKING SCREW AND DRIVER ARRANGEMENT

BACKGROUND OF THE INVENTION

A surgical locking screw and driver is described within U.S. Pat. No. 6,755,836 entitled "Bone Screw Fastener and Apparatus for Inserting and Removing Same".

This arrangement utilizes a surgical screw and driver whereby the end of the driver is moved in the horizontal plane in a forward direction within the slotted end of the surgical screw and a locking pin on the end of the driver is repeatedly rotated clockwise, via a first handle arrangement on the driver, into a threaded opening on the slotted end of the surgical screw to fasten the screw to the driver.

The driver/screw combination is then rotated clockwise, via a second handle arrangement on the driver, to attach the screw to an object.

Once the screw becomes attached thereto, the first handle arrangement on the driver is repeatedly rotated counterclockwise to release the locking pin from the surgical screw and the driver is again moved in the horizontal plane in a reverse direction from within the slotted end of the surgical screw to remove the end of the driver therefrom.

In view of surgical space limitations and surgical time requirements, it would be highly advantageous to insert the end of the driver in the downward vertical plane directly within the slotted end of the surgical screw and to attach the locking pin, on the end of the driver, to the slotted end of the surgical screw with a quarter turn clockwise rotation of the first handle arrangement on the driver to fasten the screw to the driver and a quarter turn counterclockwise rotation of the first handle arrangement on the driver to release the locking pin from the slotted end of the surgical screw, whereby the end of the driver is released from the surgical screw by movement of the end of the driver in the upward vertical plane.

One purpose of the instant invention accordingly, is to describe means whereby the end of a driver is directly inserted and removed from the slotted end of a surgical screw and is quickly attached thereto and removed therefrom.

SUMMARY OF THE INVENTION

A surgical screw and driver arrangement whereby the end of the driver is vertically inserted and removed from the slotted end of the surgical screw and whereby the end of the driver is attached to and removed from the slotted end of the surgical screw by a quarter turn in the clockwise and counterclockwise directions accordingly.

The driver includes an inner shaft connecting with a center locking cam at one end of the driver and an outer shaft that connects with a pair of blades, one on each side of the locking cam.

The surgical screw includes a slotted head at one end and a tapered threaded rod attached to the head. A pair of dovetail slots within the slotted head receive the locking cam when the driver inner shaft is rotated a quarter turn clockwise to fasten the surgical screw to the end of the driver, whereby the surgical screw rotates in conjunction with the rotation of the driver blades to threadingly advance the surgical screw within an object.

When the surgical screw is fixedly attached to the object, the inner shaft is rotated in the counterclockwise direction to release the locking cam from the dovetail slots thereby allowing the driver blades to release from the surgical screw when the end of the driver is vertically withdrawn from the slotted end thereof.

DESCRIPTION OF THE PREFERRED EMBODIMENT

Figure 1:
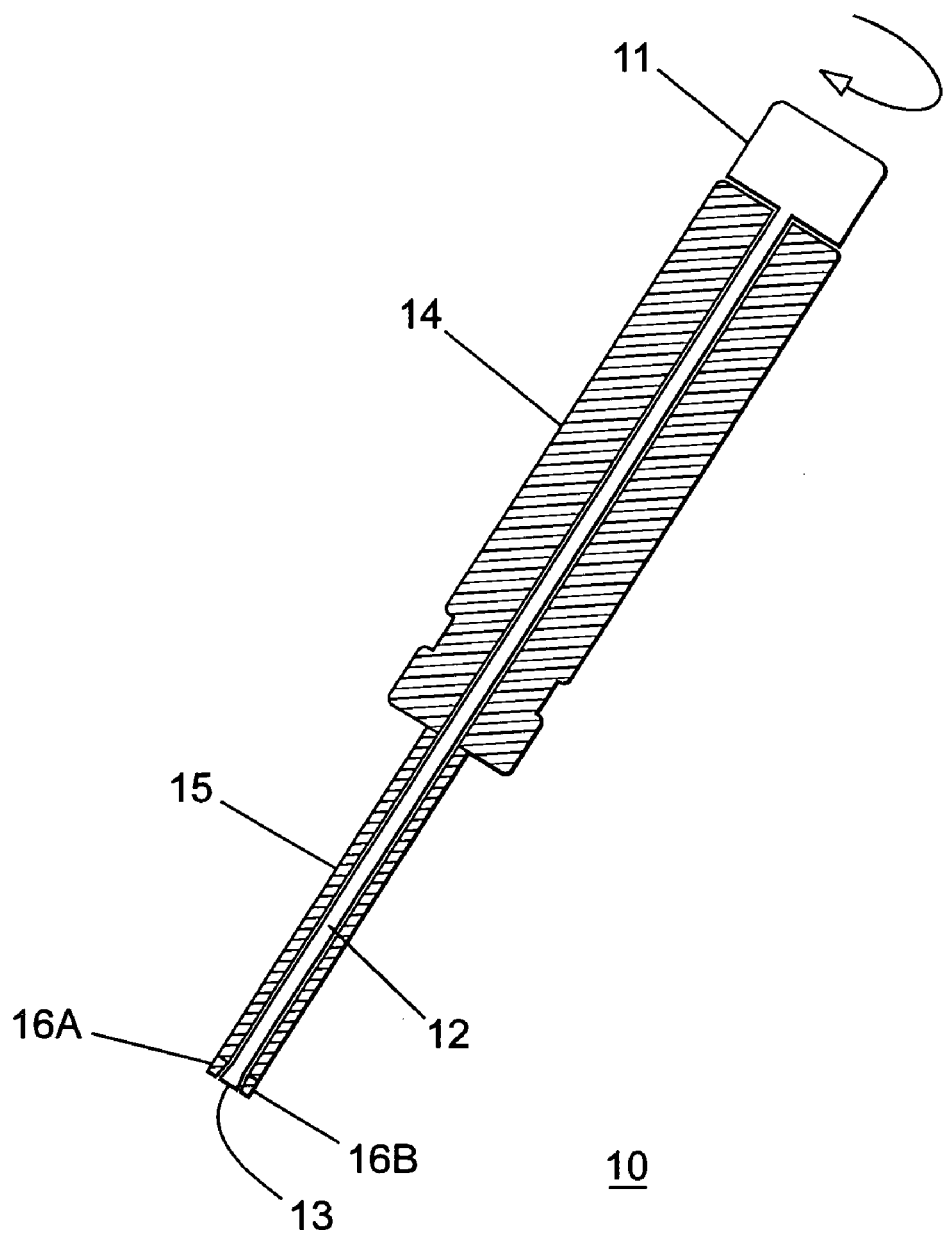
FIG. 1 is a front planar view, in partial section, of the driver according to the invention.

The driver 10 according to the invention is depicted in FIG. 1 and includes a locking handle 11 attached to an extending rod 12 terminating at a locking cam 13. A drive handle 14 surrounds the rod 12 and includes a tube 15 terminating in a pair of opposing blades 16A, 16B whereby the locking handle 11 independently controls the positioning of the locking cam 13 and the drive handle 14 independently controls the positioning of the blades 16A, 16B.

Figure 2:
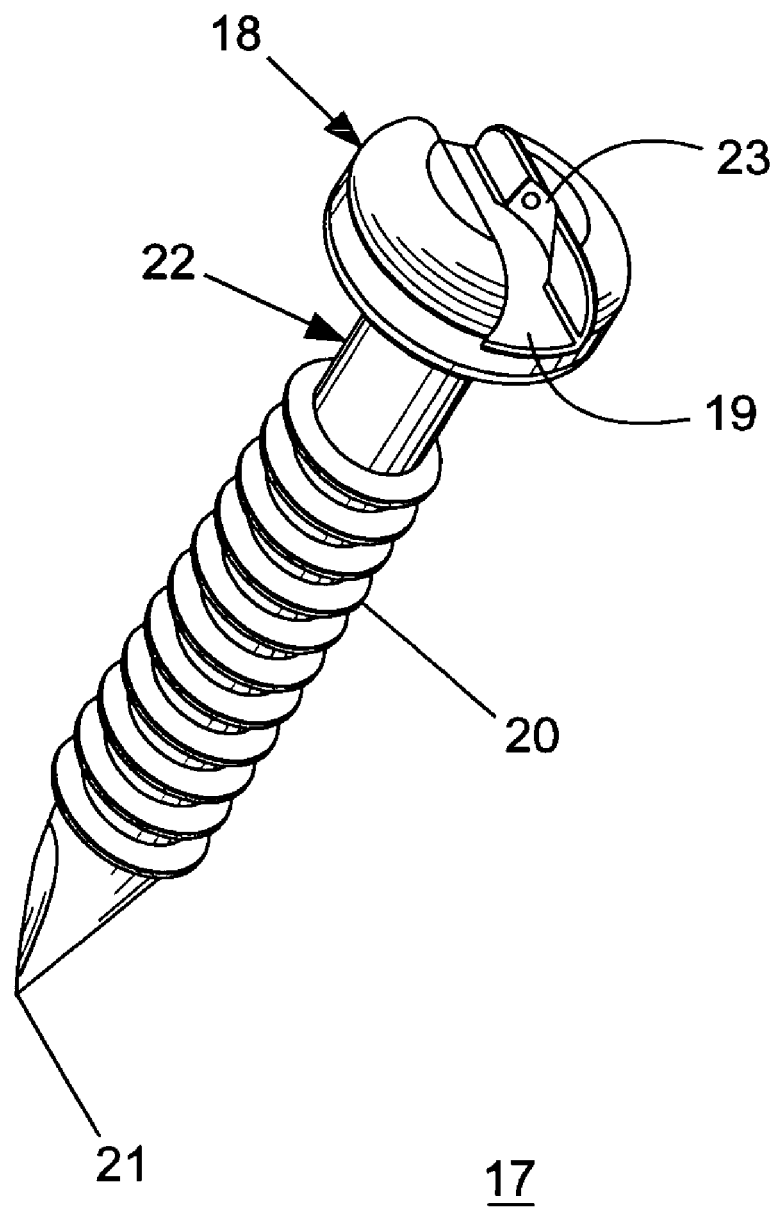
FIG. 2 is top perspective view of the surgical screw of the invention used with the driver of FIG. 1.

The surgical screw 17 used with the driver 10 of FIG. 1 is depicted in FIG. 2 and includes a cylindrical head 18 with a slot 19 extending therethru, hereafter "extending slot". A transverse dovetail receiving slot 23, hereafter "dovetail slot" is included within the head 18 for purposes to be described below in greater detail. As described in the aforementioned U.S. Pat. No. 6,755,836, the surgical screw 17 includes a shaft 22 that includes a plurality of threads 20 terminating in a pointed end 21.

Figure 3A:
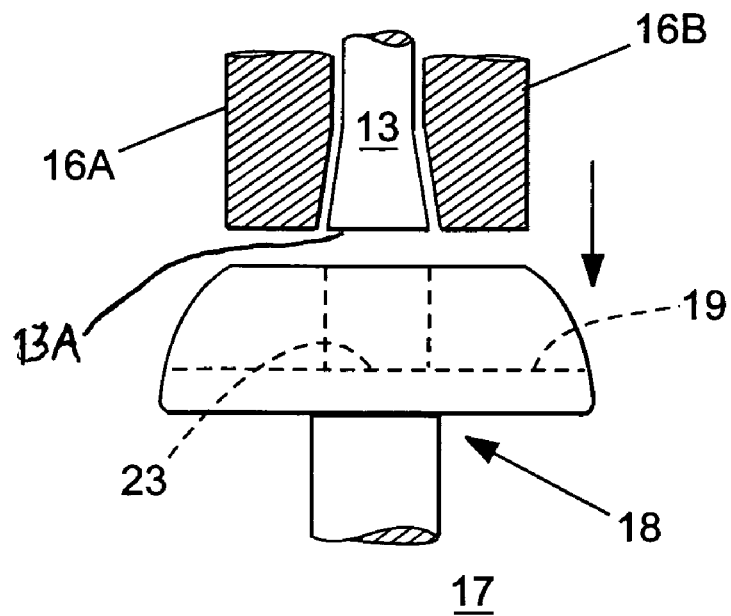
FIG. 3A is an enlarged front planar view of the end of the driver of FIG. 1 in partial section prior to insertion within the surgical screw of FIG. 2.

The blades 16A, 16B and the intermediate locking cam 13 are shown in FIG. 3A prior to insertion within the extending slot 19 and dovetail slot 23 on the head 18 of the surgical screw 17. It is noted that the locking cam 13 includes a dovetail end 13A to be received within the complimentary dovetail slot 23.

Figure 3B:
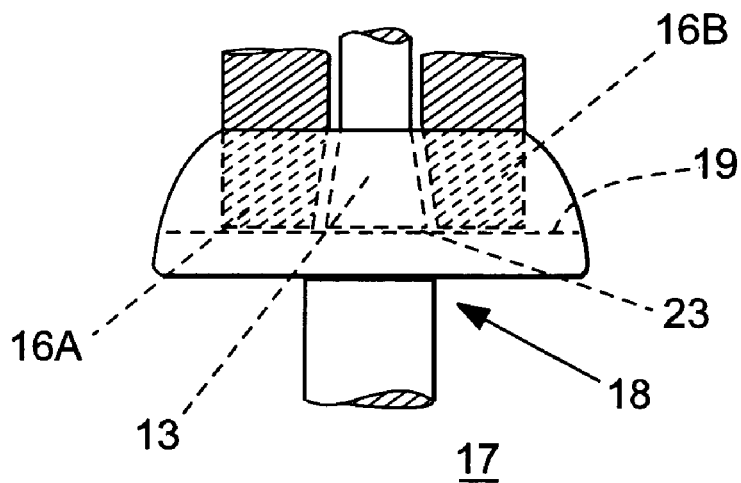
FIG. 3B is an enlarged front planar view of the end of the driver of FIG. 1 in partial section inserted within the surgical screw of FIG. 2.

The blades 16A, 16B and locking cam 13 are depicted in FIG. 3B, within the extending slot 19 such that the locking cam 13 is proximate the dovetail slot 23 within the head 18 of the surgical screw 17.

Figure 4A:
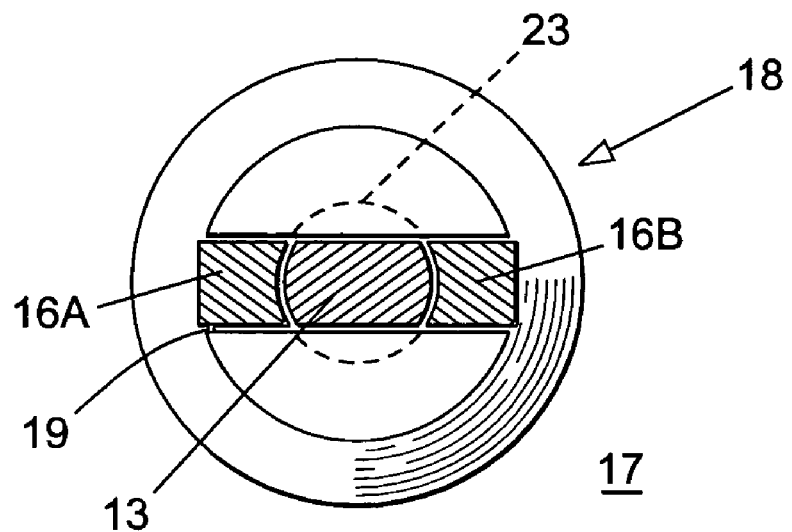
FIG. 4A is an enlarged top view of the end of the driver of FIG. 1 arranged in an unlocked condition within the surgical screw of FIG. 2.

The blades 16A, 16B and locking cam 13 are now depicted in FIG. 4A, within the extending slot 19 such that the locking cam 13 is proximate the dovetail slot 23 within the head 18 of the surgical screw 17 to show that the blades 16A, 16B and locking cam 13 can be retracted from the extending slot thereby allowing the driver 10 of FIG. 1 to be easily removed from the surgical screw 17 of FIG. 2.

Figure 4B:
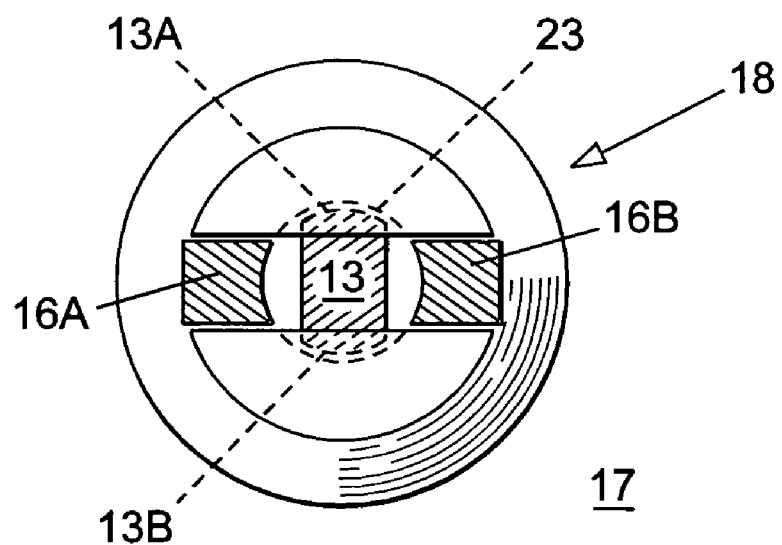
FIG. 4B is an enlarged top view of the end of the driver of FIG. 1 arranged in a locked condition within the surgical screw of FIG. 2.

To secure the surgical screw 17 to the driver 10 of FIG. 1, the locking handle 11, is rotated a quarter turn in the clockwise indicated direction, which positions the dovetail ends 13A, 13B of the locking cam 13 within the dovetail slot 23 to form a mortise joint in head 18 as best seen in FIG. 4B. This now allows the blades 16A, 16B to rotate surgical screw 17 in either direction in response to the rotation of the drive handle 14 on the driver 10 of FIG. 1, without losing contact with the surgical screw.

When the surgical screw 17 is attached to an object, such as a patient's bone (not shown), for example, the locking handle 11, on the driver 10 of FIG. 1 is rotated a quarter turn in the counterclockwise direction to move the locking cam 13 from the locked position shown within the dovetail slot 23 of FIG. 4B to the unlocked position free of the dovetail slot 23, as shown in FIG. 4A.

A surgical screw and driver arrangement has herein been described whereby the driver blades are downward vertically inserted within the surgical screw slot and the screw is retained by the driver by a simple clockwise quarter turn of the driver locking handle until the screw is fastened to a targeted object, and is released froth the driver by a simple counterclockwise quarter turn of the driver locking handle to thereby allow removal of the driver from the surgical screw by upwardly removing the driver blades therefrom.

What is claimed is:

1. A driver for attaching and removing a screw to and from an object comprising:
   a lock handle having a rod extending from one end of said lock handle and a locking cam rotatably attached to an end of said rod;
   a drive handle proximate said lock handle, wherein said lock handle and said drive handle define a common rotational axis, and wherein said lock handle and said drive handle are independently rotatable with respect to one another about said common rotational axis, said drive handle having a tube extending from one end and a pair of fastening blades fixedly attached to an end of said tube, said locking cam being arranged intermediate said pair of fastening blades, wherein said rod extends within said drive handle and said tube and whereby said lock handle locks and unlocks said locking cam from said screw and said drive handle fastens said screw to an object, and wherein said locking cam comprises a dovetail configuration.

2. A driver for attaching and removing a screw to and from an object comprising:
   a lock handle having a rod extending from one end of said lock handle and a locking cam rotatably attached to an end of said rod;
   a drive handle proximate said lock handle, wherein said lock handle and said drive handle define a common rotational axis, and wherein said lock handle and said drive handle are independently rotatable with respect to one another about said common rotational axis, said drive handle having a tube extending from one end and a pair of fastening blades fixedly attached to an end of said tube, said locking cam being arranged intermediate said pair of fastening blades, wherein said rod extends within said drive handle and said tube and whereby said lock handle locks and unlocks said locking cam from said screw and said drive handle fastens said screw to an object, and wherein said screw includes first slot means for accepting said fastening blades, and wherein said screw includes second slot means transverse to said first slot means, said second slot means arranged in a dovetail configuration for accepting said locking cam.

* * * * *